United States Patent [19]

Habib et al.

[11] 4,438,020

[45] Mar. 20, 1984

[54] CATALYST SUITABLE FOR PREPARING ALDEHYDES

[75] Inventors: Mohammad M. Habib, Allison Park; Wayne R. Pretzer, Gibsonia, both of Pa.

[73] Assignee: Gulf Research & Development Company, Pittsburgh, Pa.

[21] Appl. No.: 417,534

[22] Filed: Sep. 13, 1982

Related U.S. Application Data

[63] Continuation-in-part of Ser. No. 289,404, Aug. 3, 1981, Pat. No. 4,361,706.

[51] Int. Cl.$^3$ ............................................. B01J 31/02
[52] U.S. Cl. .................................. 252/162; 252/155; 568/487; 568/902
[58] Field of Search ...................... 252/431 P, 429 B; 260/439 R

[56] References Cited

U.S. PATENT DOCUMENTS

| | | | |
|---|---|---|---|
| 4,218,340 | 8/1980 | Holmes | 252/431 P X |
| 4,253,987 | 3/1981 | Fiato | 252/431 P X |
| 4,262,154 | 4/1981 | Gane et al. | 568/487 X |
| 4,346,020 | 8/1982 | Pretzer et al. | 252/431 P X |

*Primary Examiner*—Helen M. S. Sneed
*Attorney, Agent, or Firm*—Deane E. Keith; Forrest D. Stine; Joseph J. Carducci

[57] ABSTRACT

A catalyst particularly suitable for selectively producing aldehydes, particularly acetaldehyde, which comprises (1) cobalt, (2) iodine and (3) a ligand containing atoms from Group VB of the Periodic Table separated by a sterically constrained carbon-carbon bonding.

34 Claims, No Drawings

CATALYST SUITABLE FOR PREPARING ALDEHYDES

BACKGROUND OF THE INVENTION

This application is a continuation-in-part application of our application Ser. No. 289,404 for Process for Preparing Aldehydes filed Aug. 3, 1981, now U.S. Pat. No. 4,361,706.

1. Field of the Invention

This invention is directed to a catalyst particularly suitable for selectively producing aldehydes, particularly acetaldehyde, which comprises (1) cobalt, (2) iodine and (3) a ligand containing atoms from Group VB of the Periodic Table separated by sterically constrained carbon-carbon bonding.

2. Description of the Invention

In European Patent Application No. 79302053.8, filed in the names of B. R. Gane and D. G. Stewart and published on Apr. 30, 1980, it is disclosed that when methanol is reacted with synthesis gas in the presence of a catalyst comprising (a) cobalt, (b) an iodide or a bromide and (c) a polydentate ligand, wherein the donor atoms are exclusively phosphorus, the product obtained will contain a substantial proportion of ethanol. When the polydentate ligand used is one wherein at least one of the donor atoms is phosphorus and another is aresenic, it is alleged by Gane et al. that the product will contain a mixture of ethanol and acetaldehyde.

SUMMARY OF THE INVENTION

We have found that if we introduce into a reaction zone containing (1) methanol, (2) carbon monoxide, and (3) hydrogen, a novel catalyst system containing (1) cobalt, (2), iodine and (3) a ligand containing atoms from Group VB (that is, phosphorus, arsenic and antimony) of the Periodic Table separated by sterically constrained carbon-carbon bonding, while controlling the proportion of the reaction components and the reaction parameters, we can obtain a reaction product predominating in aldehydes, including compounds convertible thereto, particularly acetaldehyde. By "compounds convertible thereto" we mean to include acetals, such a dimethyl acetal. In general the reaction product will contain at least about 30 weight percent, especially from about 35 to about 85 weight percent, of aldehydes and compounds convertible thereto. The acetaldehyde content of the reaction product will be at least about 25 weight percent, especially about 27 to about 75 weight percent. At the same time, the alcohol content of the reaction product, including compounds convertible thereto, will be very small. By "compounds convertible thereto", in the latter instance, we mean to include acetates, such as ethyl acetate. In general the reaction product will contain less than about 23 weight percent of alcohols and compounds convertible thereto, but more often from about two to about ten weight percent of alcohols and compounds convertible thereto. As to the ethanol content of the reaction product, it will be less than about 18 weight percent, but more often in the range of about 0 to about seven weight percent. The compounds referred to above that can be converted to aldehydes or alcohols can be converted thereto by any known or suitable process, for example, by hydrolysis, that is, contacting a precursor thereof with water, with or without an acid (sulfuric) or a basic (sodium hydroxide) catalyst.

As noted, the ligand component of the novel catalyst system defined and claimed herein contains atoms from Group VB of the Periodic Table. As pointed out above, by "Group VB atoms" we mean to include phosphorus, arsenic, and antimony. by "sterically constrained carbon-carbon bonding" we mean to include carbon-carbon bonding which is part of an organic divalent, trivalent or tetravalent radical, whereas a component of the bonding between these radical centers possesses a constrained geometry and a fixed spatial arrangement; this constrained geometry between these carbon atoms can be introduced by either bond unsaturation or by their incorporation into an alicyclic ring system. By "bond unsaturation" we mean to include an alkylene bond, such as

and an arylene bond, such as:

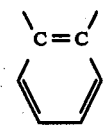

or an acetylenic bond such as —C≡C— wherein any of the above-defined R substituents can be hydrogen, a hydrocarbyl, such as defined hereinafter, a halogen, such as chlorine or bromine, a sulfur-containing substituent, such as a sulfonato group, a nitrogen-containing substituent, such as a nitro group or an amino group, an oxygen-containing substituent, such as a hydroxyl group, etc. By "cyclic ring system" we mean to include alicyclic compounds, such as cycloparaffins, cycloolefins, and cycloacetylenes; condensed aromatics; and heterocycles which can be monocyclic, bicyclic, or tricyclic ring systems in which each component ring of the system comprises a three- to eight-membered ring and can be the same or different from the other component rings in the system. The ring skeleton atoms of these systems can be substituted with hydrogen; a hydrocarbyl, such as defined hereinafter; a halogen, such as chlorine or bromine; a sulfur containing substituent, such as a sulfonato group; a nitrogen-containing substituent, such as a nitro group; and oxygen-containing substituent such as a hydroxyl group, etc.

Especially preferred ligands for use herein can be defined by the following formula:

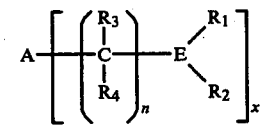

wherein $R_1$ and $R_2$, either alike or different members selected from the group consisting of alkyl radicals having from one to 24 carbon atoms, preferably from two to 10 carbon atoms; aryl radicals having from six to 20 carbon atoms, preferably from six to 10 carbon atoms; alkenyl radicals having from two to 30 carbon atoms, preferably from two to 20 carbon atoms; cycloalkyl radicals having from three to 40 carbon atoms, preferably from three to 30 carbon atoms; and aralkyl and alkaryl radicals having from six to 40 carbon atoms, preferably from six to 30 carbon atoms, preferably aryl or alkyl; $R_3$ and $R_4$ are either alike or different members selected from $R_1$ and $R_2$, defined above, and hydrogen, preferably hydrogen or alkyl; E can be phosphorus, arsenic, or antimony, preferably with each E being phosphorus or arsenic, most preferably with each E being phosphorus; and n being an integer ranging from 0 to 2, preferably from 0 to 1, provided that the sum of all n's=0–4, preferably 0–2; x is an integer equal to 2, 3 or 4; and A can be an organic divalent, trivalent or tetravalent radical when x is respectively 2, 3 or 4, whereas the bonding between these radical centers possesses a constrained geometry and a fixed spatial arrangement; moreover every E, as defined above, and which are bonded to these radical centers and as part of this constrained arrangement, can bond to the same metal atom. This constrained geometry between these centers can be introduced by bond unsaturation, e.g. aromatic, heterocyclic, olefinic, or acetylenic, or by their incorporation into cyclic ring systems comprising monocyclic, bicyclic or tricyclic systems, with each system possessing three- to eight-membered rings. When A is an alicyclic group or includes an alkylene linkage, the bidentate ligand includes cis-type and trans-type steric isomers. In the present invention, both isomers can be used. Included among the ligands that can be employed herein, are those defined below in Table I, referring to the structural formula hereinabove defined.

TABLE I

| | $R_1$ | $R_2$ | $R'_1$ | $R'_2$ | $R_3$ | $R_4$ | $R'_3$ | $R'_4$ | E | E' | A | x | n |
|---|---|---|---|---|---|---|---|---|---|---|---|---|---|
| 1. | Phenyl | Phenyl | Phenyl | Phenyl | — | — | — | — | P | P | 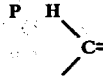 | 2 | 0 |
| 2. | Phenyl | Phenyl | Phenyl | Phenyl | H | H | H | H | P | P | " | 2 | 1 |
| 3. | Ethyl | Ethyl | Ethyl | Ethyl | — | — | — | — | P | P | " | 2 | 0 |
| 4. | Phenyl | Phenyl | Phenyl | Phenyl | — | — | — | — | P | P | 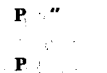 | 2 | 0 |
| 5. | Phenyl | Phenyl | Phenyl | Phenyl | H | H | H | H | P | P | " | 2 | 1 |
| 6. | Phenyl | Phenyl | Phenyl | Phenyl | $CH_3$ | H | H | H | P | P | " | 2 | 1 |
| 7. | Phenyl | Phenyl | Phenyl | Phenyl | $CH_3$ | H | $CH_3$ | H | P | P | " | 2 | 1 |
| 8. | Phenyl | Phenyl | Ethyl | Ethyl | — | — | — | — | P | P | " | 2 | 0 |
| 9. | Phenyl | Phenyl | Ethyl | Ethyl | $CH_3$ | H | H | H | P | As | " | 2 | 1 |
| 10. | Phenyl | Phenyl | Phenyl | Phenyl | — | — | — | — | As | As | " | 2 | 0 |
| 11. | Phenyl | Phenyl | Phenyl | Phenyl | — | — | — | — | P | P | 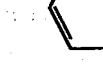 | 2 | 0 |
| 12. | Phenyl | Phenyl | Phenyl | Phenyl | — | — | — | — | P | As | " | 2 | 0 |
| 13. | Phenyl | Phenyl | Phenyl | Phenyl | — | — | — | — | P | P | 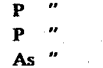 | 2 | 0 |
| 14. | Phenyl | Phenyl | Phenyl | Phenyl | — | — | — | — | P | P | 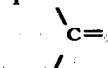 | 2 | 0 |
| 15. | Phenyl | Phenyl | Phenyl | Phenyl | — | — | — | — | P | P | 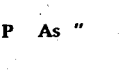 | 2 | 0 |
| 16. | Phenyl | Phenyl | Ethyl | Ethyl | H | H | H | H | P | P | " | 2 | 1 |

TABLE I-continued

| | $R_1$ | $R_2$ | $R'_1$ | $R'_2$ | $R_3$ | $R_4$ | $R'_3$ | $R'_4$ | E | E' | A | x | n |
|---|---|---|---|---|---|---|---|---|---|---|---|---|---|
| 17. | Phenyl | Phenyl | Ethyl | Ethyl | H | H | H | H | P | P | 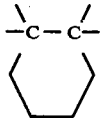 | 2 | 1 |
| 18. | Phenyl | Phenyl | Phenyl | Phenyl | H | H | H | H | P | P |  | 2 | 2 |
| 19. | Phenyl | Phenyl | Phenyl | Phenyl | — | — | — | — | P | P |  | 2 | 0 |
| 20 | Phenyl | Phenyl | Phenyl | Phenyl | — | — | — | — | P | P | —C≡C— | 2 | 0 |
| 21. | Phenyl | Phenyl | Phenyl | Phenyl | H | H | H | H | P | P | " | 2 | 2 |
| 22. | Phenyl | Phenyl | Phenyl | Phenyl | — | — | — | — | P | P | 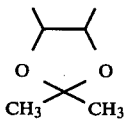 | 2 | 0 |
| 23. | Phenyl | Phenyl | Phenyl | Phenyl | H | H | H | H | P | P | " | 2 | 1 |
| 24. | Phenyl | Phenyl | Phenyl | Phenyl | — | — | — | — | P | P |  | 2 | 0 |
| 25. | Phenyl | Phenyl | Phenyl | Phenyl | H | H | H | H | P | P | " | 2 | 1 |
| 26. | Phenyl | Phenyl | Phenyl | Phenyl | — | — | — | — | P | P | 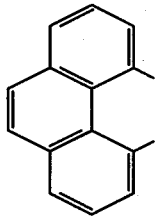 | 2 | 0 |
| 27. | Phenyl | Phenyl | Phenyl | Phenyl | — | — | — | — | P | P | 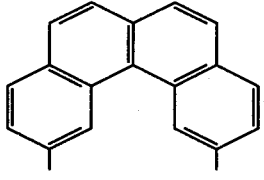 | 2 | 0 |
| 28. | Phenyl | Phenyl | Phenyl | Phenyl | H | H | H | H | P | P | " | 2 | 1 |
| 29. | Phenyl | Phenyl | Phenyl | Phenyl | — | — | — | — | P | P | " | 2 | 0 |
| 30. | Phenyl | Phenyl | Phenyl | Phenyl | H | H | H | H | P | P | " | 2 | 1 |

Any source of iodine which is capable of dissociating, that is, ionizing to form free iodide ions in the reaction medium, can be used in the present invention. Illustrative examples of iodine compounds especially suitable for use herein include iodine, potassium iodide, calcium iodide, sodium iodide, lithium iodide, aluminum iodide, bismuth iodide, hydrogen iodide, methyl iodide, ethyl iodide, tetraalkyl ammonium iodide, tetraalkyl phosphonium iodide, tetraarylphosphonium iodide, etc., and mixtures thereof.

The cobalt entity suitable for use herein can be defined as being a cobalt carbonyl, a hydrido cobalt carbonyl or a cobalt-containing compound convertible to a cobalt carbonyl or a hydrido cobalt carbonyl. By "cobalt carbonyl" we intend to define a compound containing only cobalt and carbon monoxide, such as $Co_2(CO)_8$ or $Co_4(CO)_{12}$. By "hydrido cobalt carbonyl" we intend to define a compound containing only cobalt, carbon monoxide and hydrogen, such as $HCo(CO)_4$. By "cobalt-containing material convertible to a cobalt carbonyl or a hydrido cobalt carbonyl" we intend to define any material which when mixed with hexane and subjected to 4000 pounds per square inch gauge (27.6 MPa) in an atmosphere containing hydrogen and carbon monoxide in a molar ratio of 1:1 at 150° to 200° C. for a period of three hours will result in the formation of a cobalt carbonyl, a hydrido cobalt carbonyl or mixtures thereof. Specific examples of a cobalt-containing material so convertible to a cobalt carbonyl or a hydrido cobalt carbonyl include cobalt (II) sulfate, cobalt oxide ($Co_3O_4$), cobalt(II)tetrafluoroborate, cobalt(II)acetate, cobalt(II)oxalate, cobalt(II)propionate, cobalt(II)octoate, cobalt(II)butyrate, cobalt(II)benzoate, cobalt(II)valerate, cobalt(II)formate, cobalt(II)cyclohexanebutyrate, cobalt(II)2-ethyl-hexaoate, cobalt(II)gluconate, cobalt(II)lactate, cobalt(II)naphthenate, cobalt(II)oleate, cobalt(II)citrate, cobalt(II)acetylacetonate, cobalt(II)iodide, etc.

The relative amounts of carbon monoxide and hydrogen employed in the homologation process using the novel catalyst herein can be varied over a wide range. However, in general, the molar ratio of carbon monoxide to hydrogen is from about 2:1 to about 1:2, preferably about 1.5:1 to about 1:1.5, but most preferably about 1.25:1 to about 1:1.25. Compounds or reaction mixtures which give rise to the formation of carbon monoxide and hydrogen under the reaction conditions defined herein can be used instead of mixtures comprising carbon monoxide and hydrogen which are used in the preferred embodiments of this invention.

In order to obtain a product herein that predominates in aldehydes, particularly acetaldehyde, the amount of cobalt employed relative to the ligand and to iodine is critical. Thus, the molar ratio of cobalt based on the element cobalt, to the ligand must be in the range of about 1:2 to about 7:1, preferably about 1:1.5 to about 4:1. The molar ratio of cobalt, based on the element cobalt, to iodine, based on the element iodine, must be in the range of about 1:1.15 to 1:15, preferably about 1:1.25 to about 1:5. Based on the methanol introduced into the system, the weight percent of combined cobalt and iodine, in their elemental form, can range from about 0.01 to about 10 percent, preferably from about 0.1 to about five percent.

The catalyst herein can be used either in a batch operation or by passing the reactants continuously through a reaction zone. In each case the reactor is provided with agitation means, and the pressure is maintained therein by the addition of hydrogen and carbon monoxide, or compounds producing hydrogen and carbon monoxide, as required. In order to facilitate the introduction of the phosphorus-containing ligand and the cobalt and iodine entities into the reaction zone and/or to facilitate recovery of the components of the reaction herein, they can be dissolved in an inert solvent, such as ethylene glycol, diethylene glycol monomethyl ether, acetone, sulfolanes, such as tetramethylene sulfone, lactones, such as γ-butyrolactone and ε-caprolactone, hydrocarbons, such as 1,2,3,4-tetrahydronaphthalene, mesitylenes, etc.

In the reaction zone the contents thereof are maintained at an elevated temperature and at an elevated critical pressure for a time sufficient to convert methanol to the desired aldehydes. The total pressure (based on hydrogen, carbon monoxide and any produced gases) must be at least about 2200 pounds per square inch gauge (15.02 MPa) but need not be in excess of about 10,000 pounds per square inch gauge (68.30 MPa). Especially desirable are pressures in the range of about 2500 pounds per square inch gauge (17.07 MPa) to about 7500 pounds per square inch gauge (51.19 MPa). Temperatures which are suitable for use using the novel catalyst herein are those temperatures which initiate a reaction between the reactants herein to selectively produce alcohols generally from about 150° to about 250° C., preferably from about 170° to about 220° C. The reaction is conducted for a time period sufficient to convert methanol to aldehydes, normally from about five minutes to about five hours, preferably from about ten minutes to about 2.5 hours.

Recovery of the desired aldehydes, for example acetaldehyde, from the reaction product can be effected in any convenient or conventional manner, for example, by distillation, at ambident pressure and about 21° C. The components will distill off in the following sequence for the desired recovery: acetaldehyde, propionaldehyde, methyl acetate, methanol, butyraldehyde, ethyl acetate, ethanol, etc.

DESCRIPTION OF PREFERRED EMBODIMENTS

A series of runs was carried out as follows.

In each of Runs Nos. 1, 3, 4 and 7, there was charged into a 300 cc. stainless steel autoclave equipped with agitation means, 100 milliliters of methanol, 10 millimols of cobaltous acetylacetonate, 10 millimols of iodine ($I_2$) and five millimols of a specific ligand containing atoms from Group VB of the Periodic Table separated by an unsaturated linkage. These ligands were as follows:
(Run No. 1) cis-bis(1,2-diphenylphosphino)ethylene;
(Run No. 3) bis(1,2-diphenylphosphino)benzene;
(Run No. 4) bis-alpha-alpha'-diphenylphosphino)-o-xylene; and
(Run No. 7) bis(diphenylphosphino)acetylene.

The reactor was next purged twice with nitrogen gas and then pressurized with carbon monoxide and hydrogen to a pressure of about half the desired reaction pressure. The system was then heated to a temperature of 200° C. and the pressure was adjusted to the reaction pressure, while maintaining selected molar ratios of carbon monoxide to hydrogen in the reaction zone, and such pressure was maintained throughout the reaction period. At the end of the reaction period the reactor contents were cooled by an internal cooling coil to about −75° C. The reactor was vented through a dry gas meter, and a gas sample was taken for mass spectral analysis; and the liquid product was then analyzed by gas choromatography. The data obtained are set forth below in Table II.

TABLE II

| Co:Ligand[a] Molar | Co:I Molar | Pressure PSIG | Reaction, Time | Percent[b] MeOH |
|---|---|---|---|---|

TABLE II-continued

| Run No. | R₁, R₂ | x | n | R₃, R₄ | A | Ratio | Ratio | CO:H₂ | (MPa) | Hours | Conversion |
|---|---|---|---|---|---|---|---|---|---|---|---|
| I | Phenyl | 2 | 0 | Hydrogen | $\begin{array}{c}H\ \ H\\|\ \ \ |\\-C=C-\end{array}$ | 2:1 | 0.5:1 | 1:1 | 4000(27.3) | 1.0 | 92.0 |
| II | Phenyl | 2 | 0 | Hydrogen | $\begin{array}{c}H\ \ H\\|\ \ \ |\\-C=C-\end{array}$ | 4:1(p) | 0.5:1 | 1:1 | 4000(27.3) | 1.0 | 93.0 |
| III | Phenyl | 2 | 0 | Hydrogen | —C=C— (cyclohexenyl) | 2:1 | 0.5:1 | 1:1 | 4000(27.3) | 1.0 | 93.0 |
| IV | Phenyl | 2 | 1 | Hydrogen | —C=C— (cyclohexenyl) | 2:1 | 0.5:1 | 1:1 | 4000(27.3) | 1.0 | 79.7 |
| V | Phenyl | 2 | 0 | Hydrogen | \C=C/ (cyclohexenyl) | 2:1(p) | 0.5:1 | 1.5:1 | 4000(27.3) | 1.0 | 90.0 |
| VI | Phenyl | 2 | 0 | Hydrogen | \C=C/ (cyclohexenyl) | 2:1(p) | 0.8:1 | 1:1 | 4000(27.3) | 1.0 | 86.0 |
| VII | Phenyl | 2 | 0 | Hydrogen | —C≡C— | 2:1 | 0.5:1 | 1:1 | 4000(27.3) | 1.0 | 61.7 |

| Run No. | Me₂O(c) | HAc(d) | MeF(e) | EtOH(f) | Et(OMe)₂(g) | EtCHO(h) | MeOAc(i) | PrCHO(j) | EtOAc(k) | HOAc(l) | Others(m) | Total Weight Percent Aldehydes(n) | Total Weight Percent Alcohols(o) |
|---|---|---|---|---|---|---|---|---|---|---|---|---|---|
| I | 3.7 | 53.8 | 0.6 | 5.5 | 0 | 0.4 | 11.5 | 17.4 | 3.8 | 0 | 3.2 | 72.6 | 5.6 |
| II | 4.8 | 41.0 | 0.2 | 0.8 | 0.8 | 0.2 | 19.7 | 19.7 | 6.3 | 3.3 | 3.2 | 64.1 | 7.9 |
| III | 1.9 | 51.2 | 0.7 | 0.5 | 3.4 | 0.4 | 15.4 | 17.3 | 6.1 | 0 | 2.7 | 69.7 | 6.6 |
| IV | 6.5 | 28.0 | 0.1 | 1.0 | 2.5 | 2.8 | 24.6 | 7.0 | 2.5 | 0 | 24.9 | 60.3 | 8.5 |
| V | 7.1 | 43.7 | 0.6 | 17.0 | 3.7 | 0.6 | 8.4 | 7.8 | 5.9 | 2.2 | 3.0 | 56.4 | 22.9 |
| VI | 2.0 | 43.7 | 0.5 | 9.0 | 1.3 | 1.0 | 19.8 | 12.7 | 8.2 | 1.0 | 0.9 | 58.2 | 17.2 |
| VII | 1.5 | 28.9 | 0 | 0 | 1.2 | 0.6 | 27.4 | 5.7 | 1.7 | 2.2 | 20.7 | 53.1 | 5.8 |

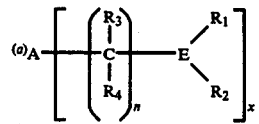

(a) $A-\left[\left(\begin{array}{c}R_3\\|\\C\\|\\R_4\end{array}\right)_n-E\begin{array}{c}R_1\\ \diagdown\\ R_2\end{array}\right]_x$ (b) Methanol
(p) Cobalt carbonyl (5.0 mmol) was used.
(c) Dimethyl ether CH₃OCH₃
(d) Acetaldehyde CH₃CO
(e) Methyl formate HCOOCH₃
(f) Ethanol C₂H₅OH
(g) Dimethyl acetal CH₃CH(OCH₃)₂
(h) Propanol C₂H₅CHO
(i) Methyl acetate CH₃COOCH₃
(j) Butanal C₃H₇CHO
(k) Ethyl acetate CH₃COOC₂H₅
(l) Actic acid CH₃COOH
(m) Mixtures of 1,1-dimethoxy ethane, 1,1-dimethoxy butane, 1,1-diethoxy ethane, diethylether, crotonaldehyde and other aldehyde condensation products
(n) Aldehydes + material convertible to aldehydes, for example, by hydrolysis
(o) Alcohols + meterials convertible to alcohols, for example, by hydrolysis The data in the above tables clearly show that when ligands defined herein are used in the claimed novel catalyst composition, a product is obtained containing the desired amounts of aldehydes, including the desired amounts of acetaldehyde.

Obviously, many modifications and variations of the invention, as hereinabove set forth, can be made without departing from the spirit and scope thereof, and therefore only such limitations should be imposed as are indicated in the appended claims.

We claim:

1. A novel catalyst composition comprising (1) cobalt, (2) iodine and (3) a ligand containing phosphorus atoms separated by a sterically constrained carbon-carbon bonding, the molar ratio of cobalt to said ligand being in the range of about 1:2 to about 7:1, and the molar ratio of cobalt to iodine being in the range of about 1:1.15 to about 1:15.

2. The novel catalyst composition of claim 1 wherein said sterically constrained carbon-carbon bond can be an alkylene bond, an arylene bond or an acetylenic bond.

3. The novel catalyst composition of claim 1 wherein said sterically constrained carbon-carbon bond is an alkylene bond.

4. The novel catalyst composition of claim 1 wherein said sterically constrained carbon-carbon bond is an arylene bond.

5. The novel catalyst composition of claim 1 wherein said sterically constrained carbon-carbon bond is an acetylenic bond.

6. The novel catalyst composition of claim 1 wherein said sterically constrained bond is incorporated into an alicyclic ring system.

7. The novel catalyst composition of claim 1 wherein the molar ratio of cobalt to said ligand is in the range of about 1:1.5 to about 4:1, and the molar ratio of cobalt to iodine is in the range of about 1:1.25 to about 1:5.

8. The novel catalyst composition of claim 1 wherein the ligand is defined by the following formula:

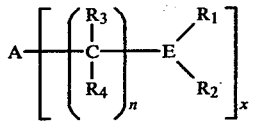

wherein $R_1$ and $R_2$ are either alike or different members selected from the group consisting of alkyl radicals having from one to 24 carbon atoms, aryl radicals having from six to 20 carbon atoms, alkenyl radicals having from two to 30 carbon atoms, cycloalkyl radicals having from three to 40 carbon atoms, and aralkyl and alkaryl radicals having from six to 40 carbon atoms; $R_3$ and $R_4$ are either alike or different members selected from the group consisting of hydrogen alkyl radicals having from one to 24 carbon atoms, aryl radicals having from six to 20 carbon atoms, alkenyl radicals having from two to 30 carbon atoms, cycloalkyl radicals having from three to 40 carbon atoms, and aralkyl and alkaryl radicals having from six to 40 carbon atoms; E is a phosphorus atom; A is an organic divalent, trivalent or tetravalent radical with the bonding between these radical centers possessing a constrained geometry and a fixed spatial arrangement, with this constrained geometry being introduced by bond unsaturation or by their incorporation into an acyclic ring system; and n is an integer ranging from 0 to 2, provided that the sum of all n's is equal to 0 to 4, and x is an integer equal to 2, 3 or 4.

9. The novel catalyst composition of claim 8 wherein $R_1$ and $R_2$ are either alike or different members selected from the group consisting of alkyl radicals having from two to ten carbon atoms, aryl radicals having from six to ten carbon atoms, alkenyl radicals having from two to 20 carbon atoms, cycloalkyl radicals having from three to 30 carbon atoms, and aralkyl and alkaryl radicals having from six to 30 carbon atoms; and $R_3$ and $R_4$ are either alike or different members selected from the group consisting of hydrogen, alkyl radicals having from two to ten carbon atoms, aryl radicals having from six to ten carbon atoms, alkenyl radicals having from two to 20 carbon atoms, cycloalkyl radicals having from three to 30 carbon atoms, and aralkyl and alkaryl radicals having from six to 30 carbon atoms.

10. The novel catalyst composition of claim 8 wherein said bond unsaturation has from two to ten carbon atoms.

11. The novel catalyst composition of claim 8 wherein said bond unsaturation has from two to six carbon atoms.

12. The novel catalyst composition of claim 8 wherein said bond unsaturation is an alkylene bond.

13. The novel catalyst composition of claim 8 wherein said bond unsaturation is an arylene bond.

14. The novel catalyst composition of claim 8 wherein said bond unsaturation is an acetylenic bond.

15. The novel catalyst composition of claim 8 wherein said bond unsaturation is incorporated into an alicyclic ring system.

16. The novel catalyst composition of claim 8 wherein $R_1$ and $R_2$ can be aryl or alkyl radicals.

17. The novel catalyst composition of claim 8 wherein $R_1$ and $R_2$ are aryl radicals.

18. The novel catalyst composition of claim 8 wherein $R_1$ and $R_2$ are alkyl radicals.

19. The novel catalyst composition of claim 9 wherein $R_1$ and $R_2$ are aryl or alkyl radicals.

20. The novel catalyst composition of claim 9 wherein $R_1$ and $R_2$ are aryl radicals.

21. The novel catalyst composition of claim 9 wherein $R_1$ and $R_2$ are alkyl radicals.

22. The novel catalyst composition of claim 9 wherein $R_3$ and $R_4$ can be hydrogen or aryl or alkyl radicals.

23. The novel catalyst composition of claim 9 wherein $R_3$ and $R_4$ are hydrogen.

24. The novel catalyst composition of claim 9 wherein $R_3$ and $R_4$ are aryl radicals.

25. The novel catalyst composition of claim 9 wherein $R_3$ and $R_4$ are alkyl radicals.

26. The novel catalyst composition of claim 9 wherein $R_1$ and $R_2$ are phenyl radicals, and $R_3$ and $R_4$ are hydrogen.

27. The novel catalyst composition of claim 8 wherein n is equal to 0; x=2; $R_1$ and $R_2$ are phenyl; and A is ethylene.

28. The novel catalyst composition of claim 9 wherein n is equal to 0; x=2; $R_1$ and $R_2$ are phenyl; and A is ethylene.

29. The novel catalyst composition of claim 8 wherein n is equal to 0; x=2; $R_1$ and $R_2$ are phenyl; and A is phenyl.

30. The novel catalyst composition of claim 9 wherein n is equal to 0; x=2; $R_1$ and $R_2$ are phenyl; and A is phenyl.

31. The novel catalyst composition of claim 8 wherein n is equal to 1; x=2; $R_1$ and $R_2$ are phenyl; $R_3$ and $R_4$ are hydrogen; and A is phenyl.

32. The novel catalyst composition of claim 9 wherein n is equal to 1; x=2; $R_1$ and $R_2$ are phenyl; $R_3$ and $R_4$ are hydrogen; and A is phenyl.

33. The novel catalyst composition of claim 8 wherein n is equal to 0; x=2; $R_1$ and $R_2$ are phenyl; and A is acetylene.

34. The novel catalyst composition of claim 9 wherein n is equal to 0; x=2; $R_1$ and $R_2$ are phenyl; and A is acetylene.

* * * * *

UNITED STATES PATENT OFFICE
CERTIFICATE OF CORRECTION

Patent No. 4,438,020                    Dated March 20, 1984

Inventor(s) Mohammed M. Habib and Wayne R. Pretzer

It is certified that error appears in the above-identified patent and that said Letters Patent are hereby corrected as shown below:

|  |  | x | n |  | x | n |
|---|---|---|---|---|---|---|

Col. 4, Table I, Item 13:  " [blank] "  should read -- 2    0 --

Col. 9, Table II, Item (g), "CH$_3$CH(OCH$_3$9$_2$" should read --CH$_3$CH(OCH$_3$)$_2$-- ;

Col. 9, Table II, Item (n), "+ material" should read -- + materials --;
Col. 9, Table II, Item (o), "+ meterial" should read -- + materials --;

Col. 9, Table II-cont'd, Item VII (about line 45) under Me$_2$O$^{(c)}$, "1.5" should read --11.5--.

Signed and Sealed this

Twenty-third Day of April 1985

[SEAL]

Attest:

DONALD J. QUIGG

Attesting Officer      Acting Commissioner of Patents and Trademarks